(12) United States Patent
Aldridge

(10) Patent No.: US 9,017,387 B2
(45) Date of Patent: Apr. 28, 2015

(54) APPARATUS AND SYSTEM FOR VERTEBRAE STABILIZATION AND CURVATURE CORRECTION, AND METHODS OF MAKING AND USING SAME

(76) Inventor: James H. Aldridge, Augusta, MI (US)

(*) Notice: Subject to any disclaimer, the term of this patent is extended or adjusted under 35 U.S.C. 154(b) by 373 days.

(21) Appl. No.: 13/217,195

(22) Filed: Aug. 24, 2011

(65) Prior Publication Data

US 2012/0253399 A1    Oct. 4, 2012

Related U.S. Application Data

(63) Continuation-in-part of application No. 13/055,817, filed on Jan. 13, 2011, which is a continuation-in-part of application No. 12/838,116, filed on Jul. 16, 2010, now Pat. No. 8,425,566.

(60) Provisional application No. 61/288,273, filed on Dec. 19, 2009.

(51) Int. Cl.
*A61B 17/70* (2006.01)

(52) U.S. Cl.
CPC ......... *A61B 17/7032* (2013.01); *A61B 17/7008* (2013.01)

(58) Field of Classification Search
CPC .................. A61B 17/7008; A61B 17/7032
USPC ......... 606/246, 250–253, 258–262, 264, 277, 606/278, 305–308, 328, 265–272
See application file for complete search history.

(56) References Cited

U.S. PATENT DOCUMENTS

| | | | |
|---|---|---|---|
| 4,048,897 A | 9/1977 | Price, Jr. | |
| 4,611,580 A | 9/1986 | Wu | |
| 4,826,376 A | 5/1989 | Aldridge et al. | |
| 5,042,982 A * | 8/1991 | Harms et al. ................... | 606/256 |
| 5,196,014 A * | 3/1993 | Lin ............................... | 606/272 |
| 5,207,678 A * | 5/1993 | Harms et al. ................... | 606/267 |
| 5,466,238 A * | 11/1995 | Lin ............................... | 606/264 |
| 5,702,392 A * | 12/1997 | Wu et al. ....................... | 606/264 |
| 6,050,766 A | 4/2000 | Kies et al. | |
| 7,060,066 B2 | 6/2006 | Zhao et al. | |
| 7,198,627 B2 | 4/2007 | Bagga et al. | |
| 7,201,753 B2 | 4/2007 | Schlapfer et al. | |
| 7,235,075 B1 * | 6/2007 | Metz-Stavenhagen ..... | 606/86 A |
| 7,722,646 B2 * | 5/2010 | Ralph et al. ................... | 606/246 |
| 8,114,133 B2 * | 2/2012 | Logan ........................... | 606/258 |
| 2003/0031531 A1 | 2/2003 | Aldridge | |
| 2006/0229607 A1 * | 10/2006 | Brumfield ....................... | 606/61 |
| 2006/0293670 A1 | 12/2006 | Smisson, III et al. | |

(Continued)

*Primary Examiner* — Jan Christopher Merene
*Assistant Examiner* — Atiya Mahmud
(74) *Attorney, Agent, or Firm* — Weiner & Burt, PC.; Irving M. Weiner; Pamela S. Burt

(57) ABSTRACT

An apparatus, system and kit of components useful as a stabilization or correction system for a spinal column, especially in the field of pediatrics. A threaded rod is used that can be straight, rigid, bent or flexible depending on the body condition to be addressed. The rod may be bent or flexible to achieve varying degrees of lordosis (backward curvature) or kyphosis (forward curvature) before being affixed to the anchoring means and apparatus. The straightness, curvature, bent, or flexibility of rod depends upon the location along the spinal column. Once installed to the vertebrae, the rod provides the proper, desired curvature and stabilization for the spinal column. Sharp edges and corners of the apparatus are eliminated by rounding the edges and corners.

3 Claims, 6 Drawing Sheets

(56) References Cited

U.S. PATENT DOCUMENTS

| | | |
|---|---|---|
| 2007/0016190 A1 | 1/2007 | Martinez et al. |
| 2008/0195153 A1 | 8/2008 | Thompson |
| 2009/0281572 A1* | 11/2009 | White .......................... 606/246 |
| 2011/0152939 A1 | 6/2011 | Aldridge |

* cited by examiner

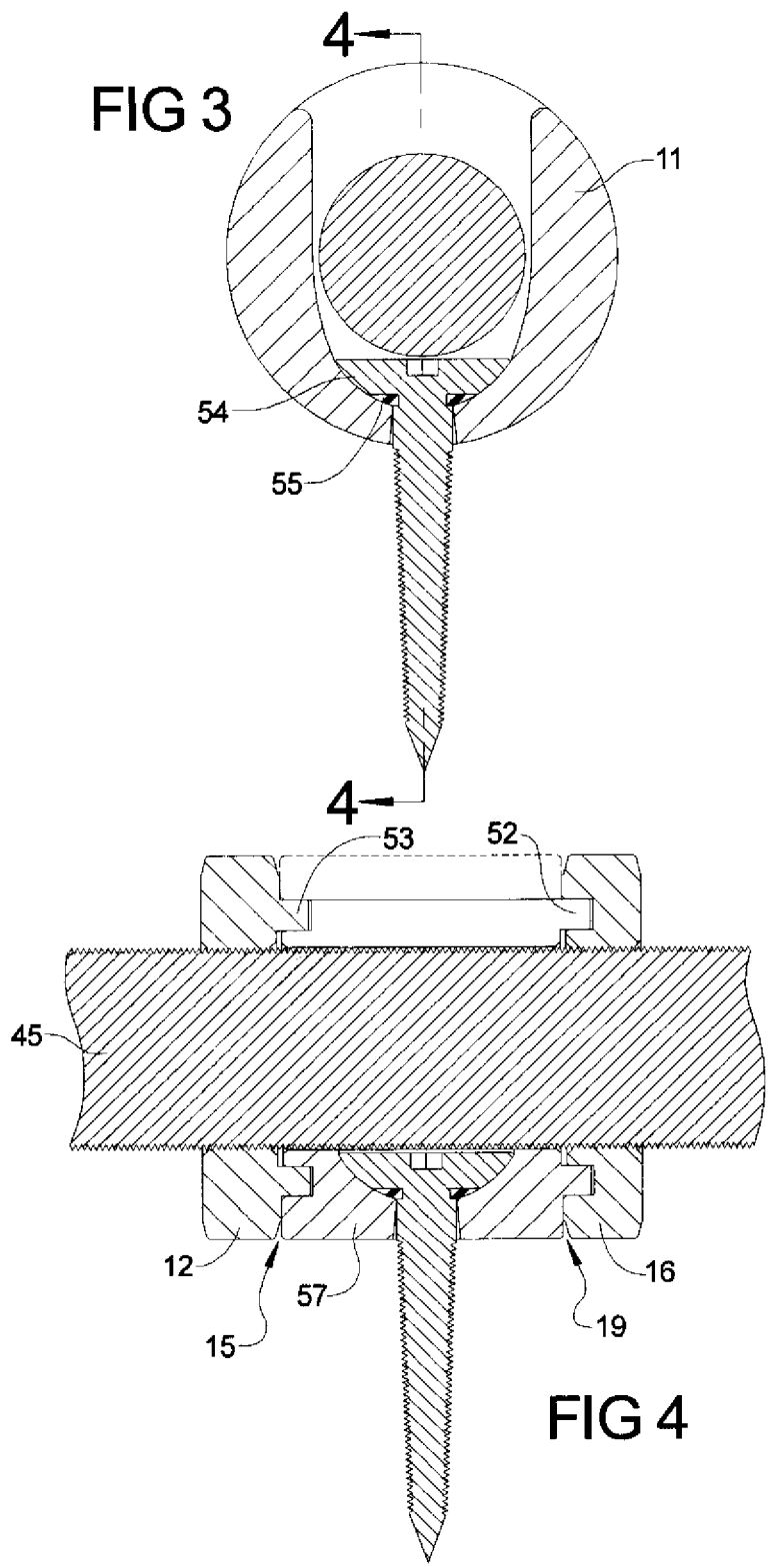

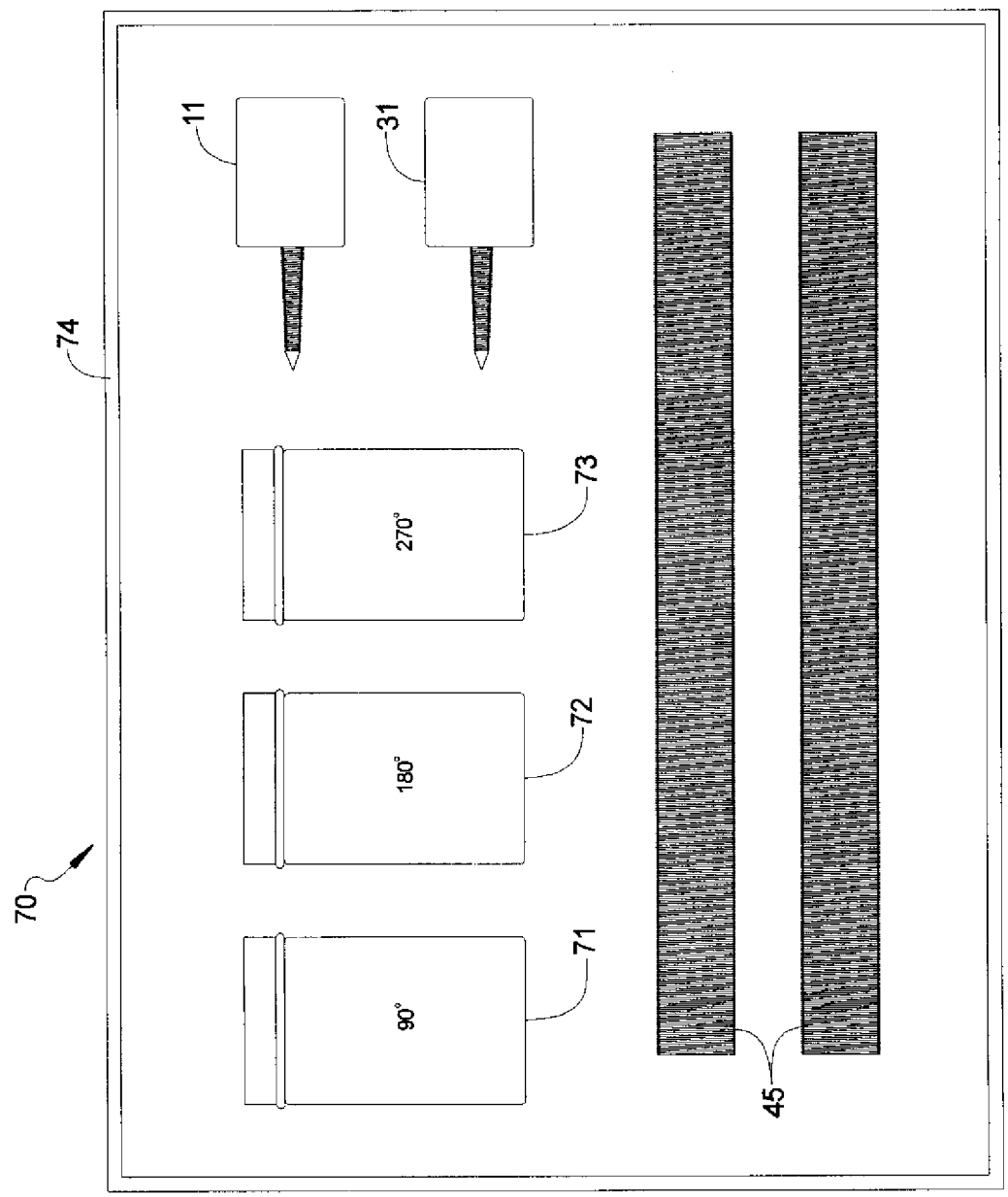

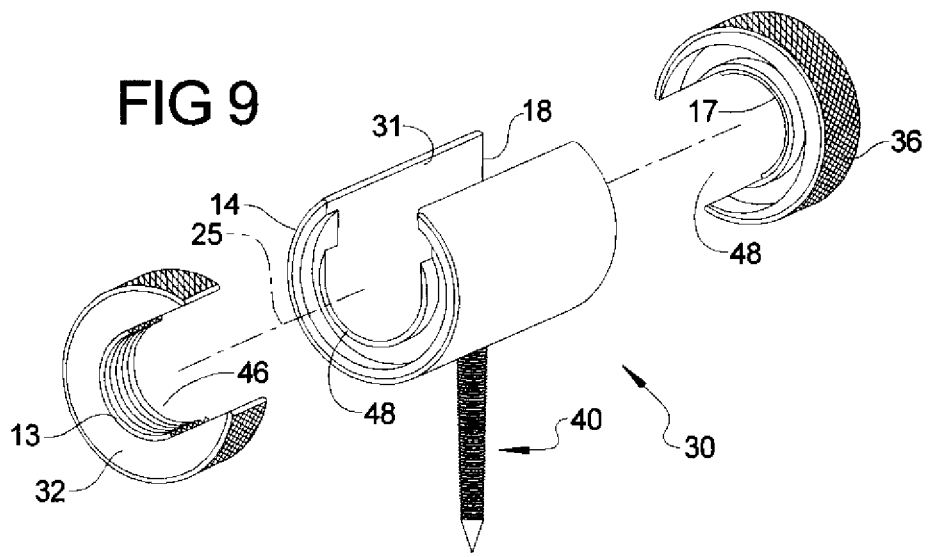
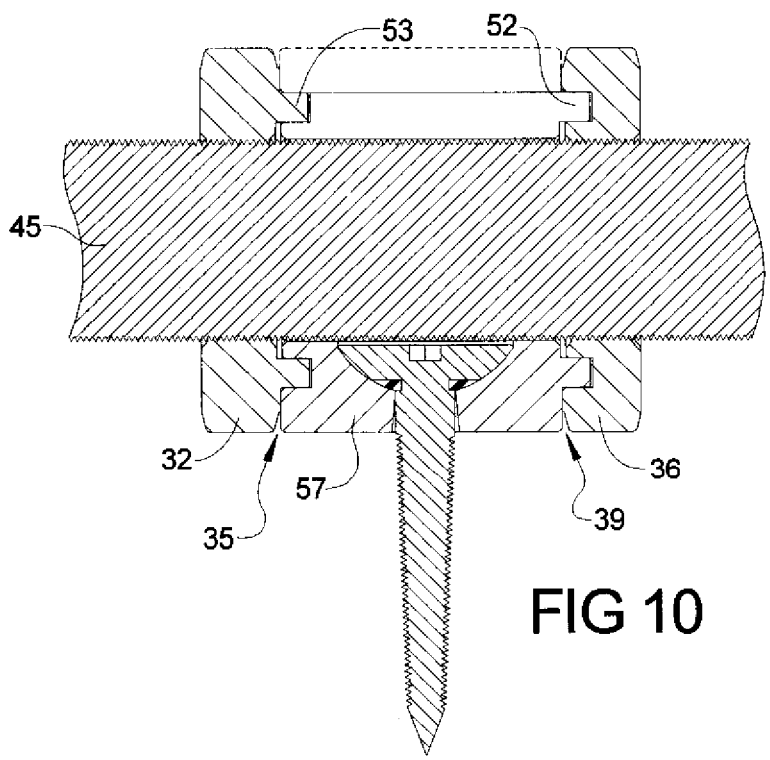

APPARATUS AND SYSTEM FOR VERTEBRAE STABILIZATION AND CURVATURE CORRECTION, AND METHODS OF MAKING AND USING SAME

The present application is a continuation-in-part of and claims priority from U.S. patent application Ser. No. 13/005,817 filed Jan. 13, 2011, which in turn is a continuation-in-part of and claims priority from U.S. patent application Ser. No. 12/838,116 filed Jul. 16, 2010 now U.S. Pat. No. 8,425,566, which in turn claims priority from and is based on U.S. Provisional Patent Application 61/288,273 filed Dec. 19, 2009.

BACKGROUND OF THE INVENTION

The present invention relates generally to an apparatus, system and kit of components for stabilizing and/or correcting the curvature of external members, and methods of making and using same.

More particularly, the present invention relates to an apparatus and system for stabilizing and/or correcting the curvature of vertebrae, and methods of making and using same, especially in the field of pediatrics.

The prior, but not necessarily relevant, art is exemplified by: Price, Jr. U.S. Pat. No. 4,048,897; Kies et al. U.S. Pat. No. 6,050,766; Zhao et al. U.S. Pat. No. 7,060,066; and Martinez et al. United States Patent Application Publication 2007/0016190.

It is a desideratum of the present invention is to avoid the animadversion, disadvantages and deficiencies of conventional devices and techniques, and to provide a novel apparatus, system and kit of components that eliminates constant, time-consuming, and difficult adjustments.

SUMMARY OF THE INVENTION

The present invention provides an apparatus, comprising: a main central member having rounded edges; an externally threaded rod member for passing through said main central member; a first generally C-shaped lock nut member having rounded edges, a partially cylindrical knurled outer surface, and an internally axial bore portion; the first generally C-shaped lock nut member being removably and selectively connectable to a first end of the main central member; first connection means axially threadedly connecting the first generally C-shaped lock nut member and the main central member preventing separation thereof; a second generally C-shaped lock nut member having rounded edges, a partially cylindrical knurled outer surface, and an internally axial bore portion; the second generally C-shaped lock nut member being removably and selectively connectable to a second end of the main central member; second connection means axially threadedly connecting the second generally C-shaped lock nut member and the main central member preventing separation thereof; an anchoring device extending from the main central member; and the anchoring device permitting anchoring the apparatus to an external or internal body part member.

The present invention also provides a system, comprising, in combination: a first apparatus having: a first main central member having rounded edges; a first generally C-shaped lock nut member having rounded edges, a partially cylindrical knurled outer surface, and an internally axial bore portion; the first generally C-shaped lock nut member being removably and selectively connectable to a first end of the first main central member; first connection means axially threadedly connecting the first generally C-shaped lock nut member and the first main central member preventing separation thereof; a second generally C-shaped lock nut member having rounded edges, a partially cylindrical knurled outer surface, and an internally axial bore portion; the second generally C-shaped lock nut member being removably and selectively connectable to a second end of the first main central member; second connection means axially threadedly connecting the second lock nut member and the first main central member preventing separation thereof; a first anchoring device extending from the first main central member; and the first anchoring device permitting anchoring the first apparatus to a first external or internal body part member; a second apparatus having: a second main central member having rounded edges; a third generally C-shaped lock nut member having rounded edges, a partially cylindrical knurled outer surface, and an internally axial bore portion; the third generally C-shaped lock nut member being removably and selectively connectable to a first end of the second main central member; third connection means axially threadedly connecting the third lock nut member and the second main central member preventing separation thereof; a fourth generally C-shaped lock nut member having rounded edges, a partially cylindrical knurled outer surface, and an internally axial bore portion; the fourth generally C-shaped lock nut member being removably and selectively connectable to a second end of the second main central member; fourth connection means for axially connecting the third generally C-shaped lock nut member and the second main central member to preventing separation thereof; a second anchoring device extending from the second main central member; and the second anchoring device permitting anchoring the second apparatus to a second external or internal body part member; an externally threaded rod member for passing through said first and second main central members; whereby the first and second body part members are constrained in a predetermined position and orientation relative to one another.

The present invention also provides a kit of components for stabilizing body parts comprising: a main housing container for holding: two main central members having rounded edges; generally C-shaped lock nut members having rounded edges, a partially cylindrical knurled outer surface, and an internally axial bore portion; an anchoring device extending from each main central member; an externally threaded rod member; and each said generally C-shaped lock nut member is fabricated and designed to threadedly tighten into a locked position by turning same by a predetermined amount which is less than one complete rotation thereof.

An object of the present invention is to provide an apparatus, system and kit of components as described hereinabove which is particularly useful as a stabilization and/or correction system for a spinal column and/or portions thereof, especially in the field of pediatrics.

Another object of the present invention is to provide an apparatus, system and kit of components as described hereinabove wherein each lock nut member is fabricated and designed to threadedly tighten into a locked position by turning same by a predetermined amount which is less than one complete rotation thereof, and to enable the surgeon to determine in which direction the slot of the locknut faces, e.g., away from fleshy areas or soft body tissue.

Another object of the present invention is to provide an apparatus, system and kit of components as described hereinabove wherein the anchoring device is rotationally connected to the main central member.

Another object of the present invention is to provide an apparatus, system and kit of components as described hereinabove wherein the main central member and the first and second generally C-shaped internally-threaded lock nuts are shaped and dimensioned to permit passage therethrough of an external threaded rod member.

Another object of the present invention is to provide an apparatus, system and kit of components described hereinabove wherein the first and second generally C-shaped internally-threaded lock nuts and the first and second connection means are shaped and dimensioned to permit passage therethrough of an externally threaded rod member, and to permit selective, adjustable and releasable attachment of the apparatus to the externally threaded rod member.

Another object of the present invention is to provide an apparatus and system as described hereinabove wherein the anchoring device is provided with means to threadedly affix the anchoring device to a body part member.

Other objects, advantages, and features of the present invention will become apparent to those persons skilled in this particular area of technology and to other persons after having been exposed to the present patent application.

BRIEF DESCRIPTION OF THE DRAWINGS

FIG. 3 is a sectional view taken along the line 3-3 in FIG. 2.

FIG. 4 is a sectional view taken along the line 4-4 in FIG. 3.

FIG. 8 is a top plan view of a kit of components in accordance with the present invention.

FIG. 9 is a perspective view of the second apparatus 30.

FIG. 10 is a section view of the second apparatus 30.

DETAILED DESCRIPTION OF THE INVENTION

Figure 1:
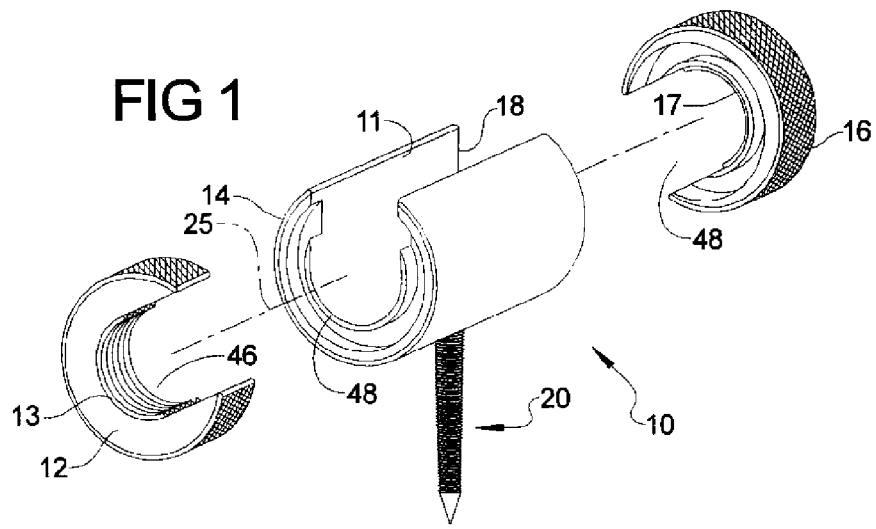
FIG. 1 is a perspective view of a preferred embodiment of the apparatus of the present invention.

With reference to the drawings, there is illustrated an apparatus 10 including: a main central member or saddle 11 having rounded edges; a first generally C-shaped internally-threaded lock nut member 12 having rounded edges and a partially cylindrical knurled outer surface, and an internally axial bore portion 13; and a second generally C-shaped internally-threaded lock nut member 16 having rounded edges and a partially cylindrical knurled outer surface, and an internally axial bore portion 17.

The first or male generally C-shaped internally-threaded lock nut member 12 may be removably attached to a first or female end 14 of the main central member 11.

The second or female generally C-shaped internally-threaded lock nut member 16 may be removably attached to a second or male end 18 of the main central member 11.

There is provided a first anchoring device 20 extending from the main central member 11.

The anchoring device 20 permits anchoring the apparatus 10 to a first external or internal body part member 26, such as a first portion 21 of a vertebrae 22.

The internally-threaded lock nut members 12 and 16 are the male and female members, respectively, or vice versa.

With reference to FIGS. 1 and 4, the internally-threaded lock nut members 12 and 16 may individually or together be threaded against the saddle 11.

This causes the members 12 and 16 and saddle 11 to be securely, but removably, axially retained to one another.

Figure 2:
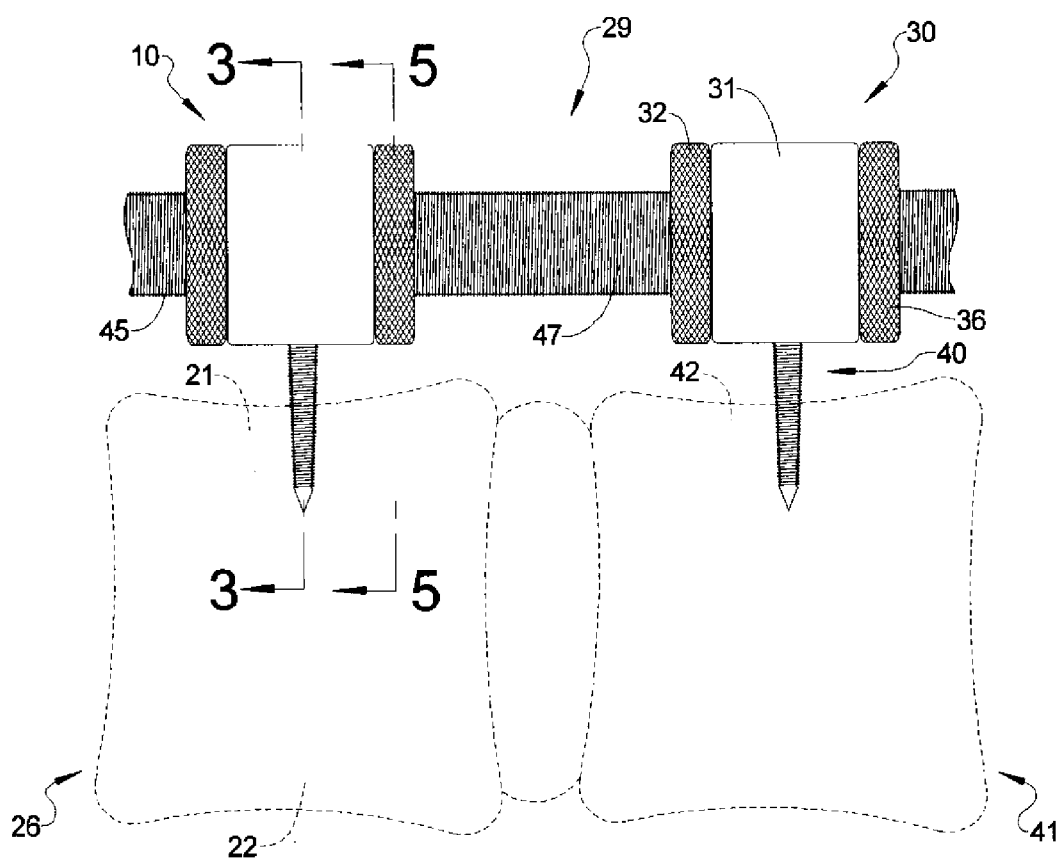
FIG. 2 is an elevational view of a preferred embodiment of the system of the present invention.

With reference to FIG. 2, the system 29 of the invention is illustrated.

System 29 includes the first apparatus 10 and a similar second apparatus 30.

With reference to FIGS. 2, 9 and 10, there is illustrated an apparatus 30 including: a main central member or saddle 31 having rounded edges; a first generally C-shaped internally-threaded lock nut member 32 having rounded edges and a partially cylindrical knurled outer surface, and an internally axial bore portion 13; and a second generally C-shaped internally-threaded lock nut member 36 having rounded edges and a partially cylindrical knurled outer surface, and an internally axial bore portion 17.

The first or male generally C-shaped internally-threaded lock nut member 32 may be removably attached to a first or female end 14 of the main central member 31.

The second or female generally C-shaped internally-threaded lock nut member 36 may be removably attached to a second or male end 18 of the main central member 31.

There is provided an anchoring device 40 extending from the main central member 31.

The anchoring device 40 permits anchoring the apparatus 30 to a second external or internal body part member 41, such as a first portion 42 of a vertebrae.

The internally-threaded lock nut members 32 and 36 are the male and female members, respectively, or vice versa.

With reference to FIGS. 9 and 10, the internally-threaded lock nut members 32 and 36 may individually or together be threaded against the saddle 31.

This causes the members 32 and 36 and saddle 31 to be securely, but removably, axially retained to one another.

Apparatus 10 has the first anchoring device 20 extending from saddle 11. Device 20 permits anchoring apparatus 10 to the first external or internal body part member 26, such as the first portion 21 of vertebrae 22.

Apparatus 30 has a second main central member or saddle 31 having rounded edges.

A third generally C-shaped internally-threaded lock nut member 32 has rounded edges, a partially cylindrical knurled outer surface, and an internally axial bore portion.

Member 32 is threadedly, but removably, connected to a first or female end of saddle 31.

A fourth generally C-shaped internally-threaded lock nut member 36 has rounded edges, a partially cylindrical knurled outer surface, and an internally axial bore portion.

Member 36 is threadedly, but removably, connected to a second or male end of saddle 31.

The internally-threaded lock nut members 32 and 36 may be the male and female members, respectively, or vice versa.

A second anchoring device 40 extends from saddle 31. Device 40 permits anchoring the second apparatus 30 to a second external or internal body member 41, such as a second portion 42 of vertebrae 22.

The system 29 constrains the first and second external or internal body members 26 and 41 in a desired predetermined position and orientation relative to one another.

The saddles 11 and 31 and the internally-threaded lock nuts 12, 16, 32 and 36 are shaped and dimensioned to permit passage therethrough of an external threaded rod member 45.

The internally-threaded lock nuts 12, 16, 32 and 36 have internal threads 46 in their respective bore portions to threadedly engage with the thread 47 of rod 45.

Saddles 11 and 31 do not have any threads whatsoever.

Figure 5:
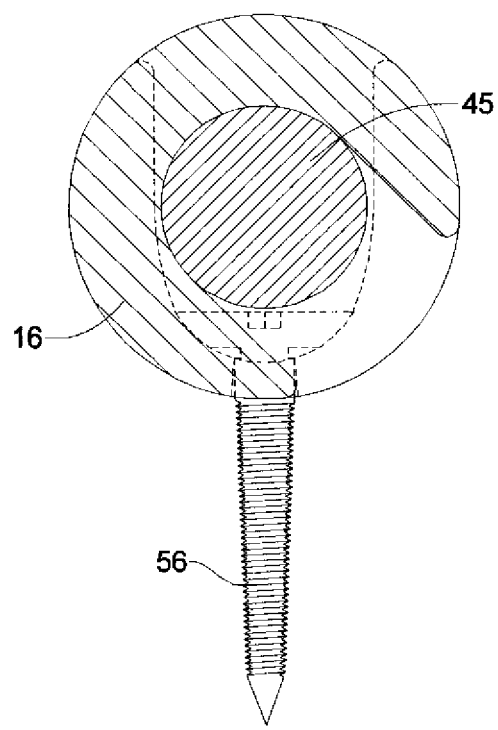
FIG. 5 is a sectional view taken along the line 5-5 in FIG. 2.
Figure 6:
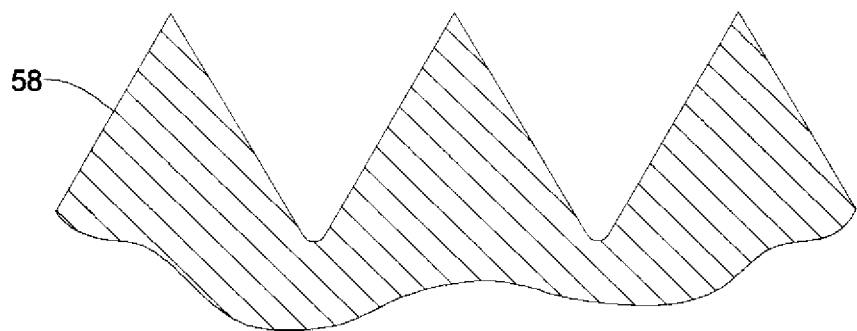
FIG. 6 is a profile of the thread of the anchoring screw.
Figure 7:
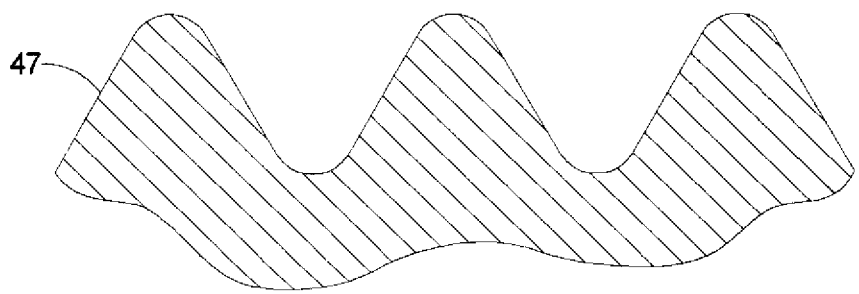
FIG. 7 is a profile of the thread of the rod.

As best seen in FIGS. 3 and 5, rod 45 does not contact saddle 11 or 31. There is a predetermined clearance between the saddle and the rod 45.

The internally-threaded lock nuts 12, 16, 32 and 36 and the connection means 15, 19, 35 and 39 are shaped and dimensioned to permit passage therethrough of threaded rod member 45, and to permit selective and releasable attachment of the apparatuses 10 and 30 to the rod member 45.

Each internally-threaded lock nut 12, 16, 32 and 36 has a slot 48.

In use, each slot 48 is positioned so that the mouth of the slot 48 is directly adjacent the rod 45 at the desired point of use, whereupon the internally-threaded lock nuts 12, 16, 32 and 36 are moved transversely on rod 45 so that the threads 46 and 47 engage. Thereafter, the internally-threaded lock nuts are rotated through a fraction of a revolution to a locked position. Removal is effected by reversing the above-described sequence.

The apparatuses 10 and 30 can be easily positioned anywhere along the length of rod 45.

The rod 45 can easily be removed from the apparatuses 10 and/or 30 or from system 29 for replacement or adjustment.

With reference to FIGS. 3, 4 and 5, the anchoring means 20 or 40 includes an enlarged top portion 54, an O-ring 55, and an elongated threaded member 56. The anchoring means 20 or 40 is rotatably supported in the lower portion 57 of its associated saddle 11 or 31, respectively.

There is also a predetermined clearance between the rod 45 and the uppermost surface of the enlarged top portion 54 of the anchoring means 20 or 40.

The elongated threaded anchoring member 36 is provided with a thread 58, and is used to be selectively and removably threadedly affixed to the external or internal body part member 26 or 41, such as vertebrae portion 21 or 42, respectively.

The O-ring 55 absorbs shocks, provides adjustability, and minimizes the possibility any breakage to other components of the apparatuses 10 or 30 and system 29. Preferably, the O-ring 55 is fabricated from a resilient and/or elastic material.

The internally-threaded lock nuts 12, 16, 32 and 36 hold the saddle 11 or 31, respectively, on the rod 45 in place.

The threads 46, 47 and 58 are provided with radius roots to increase their strength and tensile strength.

The apparatuses 10 and 30 and system 29 are particularly useful as a stabilization and/or correction system for a spinal column and/or portions thereof.

The rod 45 can be straight and rigid or somewhat flexible depending on the vertebrae condition to be addressed, and/or may have a predetermined non-straight, curved or bent shape.

For example, the rod 45 may be bent or somewhat flexible to achieve varying degrees of lordosis (backward curvature) or kyphosis (forward curvature) prior to being affixed to the anchoring means and associated apparatus.

Also, the straightness, curvature, bent, and/or flexibility of rod 45 also depends upon the location along the spinal column, i.e., the cervical region may have a kyphotic curve, while the lumbar region may have a lordotic curve. Once installed to the vertebrae, the rod 45 provides the proper, desired curvature and/or stabilization for the spinal column.

Because the apparatus 10 and 30 and system 29 may be installed in a patient, the sharp edges and corners of the apparatus are eliminated by rounding all edges and corners, and arranged so that each slot 48 is directed away from soft tissue. For example, when the apparatus is used near the cervical, the closed part of nuts 12, 16, 32 and 36 is arranged to point down to the spine.

Alternatively, internally-threaded lock nuts 12 and 32 can be female members; saddle end 14 can be a complementary male member; internally-threaded lock nuts 16 and 36 can be male members; and saddle end 18 can be a complementary female member.

The components of the invention can be sold separately, or in a kit of components 70 illustrated in FIG. 8.

The kit 70 may include a main container 74 for housing the various components.

Some of the locknuts can be fabricated to tighten with a 90 degree turn, and can be supplied in a container 71.

Some of the locknuts can be fabricated to tighten with a 180 degree turn, and can be supplied in a container 72.

Some of the locknuts can be fabricated to tighten with a 270 degree turn, and can be supplied in a container 73.

The dimensions of the yokes 11 and 31 and the rods 45 can be fabricated to be small for use in the field of pediatrics.

There have been described hereinabove only some of the many possible embodiments of the present invention which can be practiced in many different ways.

Many changes, modifications, variations, and other uses and applications will become apparent to those persons skilled in this particular area of technology and to others after having been exposed to the present patent application.

Any and all such changes, modifications, variations and other uses and applications which do not depart from the spirit and scope of the present invention are therefore covered by and embraced within the patent claims set forth hereinbelow.

The invention claimed is:

1. An apparatus for use in a patient, comprising:
a main central member having all rounded edges and no threads;
said main central member having a shape of an open-ended cylindrical tube;
said open-ended cylindrical tube being provided with an open upper section extending parallel to and co-extensive with a central elongated axis of said main central member;
an externally threaded rod member for passing through said main central member without contacting said main central member;
a first generally C-shaped one-piece lock nut member having all rounded edges, a partially cylindrical knurled outer surface, a slot, a mouth of said slot, and an internally axial bore portion;
the first generally C-shaped one-piece lock nut member being removably and selectively connectable to a first end of the main central member;
first connection means connecting the first generally C-shaped one-piece lock nut member directly to the main central member preventing separation thereof;
a second generally C-shaped one-piece lock nut member having all rounded edges, a partially cylindrical knurled outer surface, a slot, a mouth of said slot, and an internally axial bore portion;
the second generally C-shaped one-piece lock nut member being removably and selectively connectable to a second end of the main central member;
second connection means connecting the second generally C-shaped one-piece lock nut member directly to the main central member preventing separation thereof;
an anchoring device extending perpendicularly from the main central member;
the anchoring device permitting anchoring the apparatus to an external or internal body part member;
the anchoring device includes an enlarged top portion and is rotationally connected to the main central member with a predetermined clearance between said rod member and an uppermost surface of said enlarged top portion of said anchoring device;

each one-piece lock nut member is fabricated and designed to threadedly tighten into a locked position by turning same by a predetermined amount which is less than one complete rotation thereof, and said locked position being such that said mouth of said slot is configured to be directed away from soft tissue in a patient;

the anchoring device is provided with means to threadedly affix the anchoring device to the body part member;

the main central member and the first and second generally C-shaped one-piece lock nuts are shaped and dimensioned to permit passage therethrough of said externally threaded rod member;

the first and second generally C-shaped one-piece lock nuts and the first and second connection means are shaped and dimensioned to permit passage therethrough of said external threaded rod member, and to permit selective and releasable attachment of the apparatus to the externally threaded rod member; and all sharp edges and corners of the apparatus are eliminated by rounding all edges and corners.

2. A system for use in a patient, comprising, in combination:

a first apparatus having:

a first main central member having all rounded edges and no threads;

said first main central member having a shape of a first open-ended cylindrical tube;

said first open-ended cylindrical tube being provided with a first open upper section extending parallel to and co-extensive with a central elongated axis of said first main central member;

a first generally C-shaped one-piece lock nut member having all rounded edges, a partially cylindrical knurled outer surface, a slot, a mouth of said slot, and an internally axial bore portion;

the first generally C-shaped one-piece lock nut member being removably and selectively connectable directly to a first end of the first main central member;

first connection means connecting the first generally C-shaped one-piece lock nut member directly to the first main central member preventing separation thereof;

a second generally C-shaped one-piece lock nut member having all rounded edges, a partially cylindrical knurled outer surface, a slot, a mouth of said slot, and an internally axial bore portion;

the second generally C-shaped one-piece lock nut member being removably and selectively connectable directly to a second end of the first main central member;

second connection means connecting the second one-piece lock nut member directly to the first main central member preventing separation thereof;

a first anchoring device extending perpendicularly from the first main central member;

the first anchoring device permitting anchoring the first apparatus to a first external or internal body part member; and all sharp edges and corners of said first apparatus are eliminated by rounding all edges and corners;

a second apparatus having:

a second main central member having all rounded edges and no threads;

said second main central member having a shape of a second open-ended cylindrical tube;

said second open-ended cylindrical tube being provided with a second open upper section extending parallel to and co-extensive with a central elongated axis of said second main central member;

a third generally C-shaped one-piece lock nut member having all rounded edges, a partially cylindrical knurled outer surface, a slot, a mouth of said slot, and an internally axial bore portion;

the third generally C-shaped one-piece lock nut member being removably and selectively connectable directly to a first end of the second main central member;

third connection means connecting the third one-piece lock nut member directly to the second main central member preventing separation thereof;

a fourth generally C-shaped one-piece lock nut member having all rounded edges, a partially cylindrical knurled outer surface, a slot, a mouth of said slot, and an internally axial bore portion;

the fourth generally C-shaped one-piece lock nut member being removably and selectively connectable directly to a second end of the second main central member;

fourth connection means connecting the third generally C-shaped one-piece lock nut member directly to the second main central member to preventing separation thereof;

a second anchoring device extending perpendicularly from the second main central member;

the second anchoring device permitting anchoring the second apparatus to a second external or internal body part member; and sharp edges and corners of said second apparatus are eliminated by rounding all edges and corners;

an externally threaded rod member for passing through said first and second main central members without contacting either of said main central members;

each said anchoring device includes an enlarged top portion and is rotationally connected to its associated main central member with a predetermined clearance between said rod member and an uppermost surface of said enlarged top portion of said anchoring device;

each one-piece lock nut member is fabricated and designed to threadedly tighten into a locked position by turning same by a predetermined amount which is less than one complete rotation thereof, and said locked position being such that said mouth of said slot is configured to be directed away from soft tissue in a patient;

the main central members and the generally C-shaped one-piece lock nuts are shaped and dimensioned to permit passage therethrough of said externally threaded rod member;

the generally C-shaped one-piece lock nuts and the connection means are shaped and dimensioned to permit passage therethrough of the external threaded rod member, and to permit selective and releasable attachment of the apparatuses to said externally threaded rod member; and each said anchoring device is provided with means to threadedly affix the anchoring device to the body part member.

3. An apparatus for use in a patient, comprising:

a main central member having all rounded edges and no threads;

said main central member having a shape of an open-ended cylindrical tube;

said open-ended cylindrical tube being provided with an open upper section extending parallel to and co-extensive with a central elongated axis of said main central member;

an externally threaded rod member for passing through said main central member without contacting said main central member;

a first generally C-shaped one-piece lock nut member having all rounded edges, a partially cylindrical knurled outer surface, a slot, a mouth of said slot, and an internally axial bore portion;

the first generally C-shaped one-piece lock nut member being removably and selectively directly connectable to a first end of the main central member;

first connection means axially connecting the first generally C-shaped one-piece lock nut member and the main central member preventing separation thereof;

said first connection means comprising complementary male and female portions of said first one-piece lock nut member and said main central member;

a second generally C-shaped one-piece lock nut member having all rounded edges, a partially cylindrical knurled outer surface, a slot, a mouth of said slot, and an internally axial bore portion;

the second generally C-shaped one-piece lock nut member being removably and selectively directly connectable to a second end of the main central member;

second connection means axially connecting the second generally C-shaped one-piece lock nut member and the main central member preventing separation thereof;

said second connection means comprising complementary male and female portions of said second one-piece lock nut member and said main central member;

an anchoring device extending perpendicularly from the main central member;

the anchoring device permitting anchoring the apparatus to an external or internal body part member;

the anchoring device includes an enlarged top portion and is rotationally connected to the main central member with a predetermined clearance between said rod member and an uppermost surface of said enlarged top portion of said anchoring device;

said main central member, said rod member, and said generally C-shaped one-piece lock nut members being configured to enable said slot to be positioned so that said mouth of said slot is directly adjacent said rod at a desired point of use, whereupon said one-piece lock nut members are moved transversely on said rod to engage the thread of said rod, and then rotated through a fraction of a revolution to a locked position;

each one-piece lock nut member is fabricated and designed to threadedly tighten into a locked position by turning same by a predetermined amount which is less than one complete rotation thereof, and said locked position being such that said mouth of said slot is configured to be directed away from soft tissue in a patient;

the anchoring device is provided with means to threadedly affix the anchoring device to the body part member;

the main central member and the first and second generally C-shaped one-piece lock nuts are shaped and dimensioned to permit passage therethrough of said externally threaded rod member;

the first and second generally C-shaped one-piece lock nuts and the first and second connection means are shaped and dimensioned to permit passage therethrough of said external threaded rod member, and to permit selective and releasable attachment of the apparatus to the externally threaded rod member; and all sharp edges and corners of the apparatus are eliminated by rounding all edges and corners.

\* \* \* \* \*